United States Patent
Huang et al.

(10) Patent No.: US 6,923,894 B2
(45) Date of Patent: Aug. 2, 2005

(54) BIOSENSOR WITH MULTIPLE SAMPLING WAYS

(75) Inventors: Ying-Che Huang, Hsinchu (TW); Thomas Y. S. Shen, Hsinchu (TW)

(73) Assignee: Apex Biotechnology Corporation, Hsinchu (TW)

( * ) Notice: Subject to any disclaimer, the term of this patent is extended or adjusted under 35 U.S.C. 154(b) by 430 days.

(21) Appl. No.: 10/023,279

(22) Filed: Dec. 20, 2001

(65) Prior Publication Data

US 2002/0100685 A1 Aug. 1, 2002

Related U.S. Application Data

(63) Continuation-in-part of application No. 09/519,863, filed on Mar. 6, 2000.

(30) Foreign Application Priority Data

Nov. 11, 1999 (TW) .......................................... 8819683 A

(51) Int. Cl.⁷ ............................................ G01N 27/327
(52) U.S. Cl. .............................. 204/403.06; 204/403.05
(58) Field of Search ....................... 204/403.01, 403.05, 204/403.06, 403.1

(56) References Cited

U.S. PATENT DOCUMENTS

| | | |
|---|---|---|
| 5,120,420 A | 6/1992 | Nankai et al. |
| 5,628,890 A | 5/1997 | Carter et al. |
| 6,270,637 B1 * | 8/2001 | Crismore et al. ...... 204/403.04 |

* cited by examiner

Primary Examiner—Alex Noguerola
(74) Attorney, Agent, or Firm—Rothwell, Figg, Ernst & Manbeck, PC

(57) ABSTRACT

A biosensor for detecting contents of biochemical components in a sample, comprising an electrically insulating substrate, a working electrode disposed on said substrate, a reference electrode disposed on said substrate, which is spaced from said working electrode, a reaction layer disposed on said working electrode and said reference electrode, wherein said reaction layer and said electrodes form a reaction area for reacting with the sample, an electrically insulating layer disposed on said substrate and having an opening for receiving the sample, wherein said opening exposes a portion of said reaction area and the end of said opening is located at the edge of the biosensor; and a reticular covering layer which covers said opening and the end of said opening of said insulating layer wherein said reticular layer and said insulting layer form a sampling area from said reticular covering area to the edge of said biosensor.

16 Claims, 16 Drawing Sheets

(a)

(b)

(a)

(b)

BIOSENSOR WITH MULTIPLE SAMPLING WAYS

The present application is a continuation-in-part of pending application Ser. No. 09/519,863, filed Mar. 6, 2000.

BACKGROUND OF THE INVENTION

1. Field of the Invention

The present invention relates to a biosensor, and more particularly, to a current strip biosensor for detecting contents of biochemical substances.

2. Description of the Prior Art

Biochemical analyzers are generally divided into three categories: wet types, dry types, and biosensors. The wet type biochemical analyzers mix samples and reagents (usually containing color reagent) to react and then detect color difference by optical instruments, such as colorimeters or spectrophotometers. The wet type analyzers cannot use whole bloods as samples because the whole bloods need pretreatment. Furthermore, the wet type analyzers require expensive equipments and rely on professionals to operate. Therefore, they are usually applied in hospitals and inspecting centers. For the dry type biochemical analyzers, after test strip surfaces are coated with chemical reagents, enzymes, or antibodies, the test strips then contact with samples directly for analysis. Though reagent preparing processes and operations are simplified, the detection is still based on colorimetry. The test strips of the dry type analyzers are subject to oxidation and discoloration. Whole bloods still cannot be applied to the test strips because of color interference.

The biosensor is composed of a biological device, a membrane device, and a transducer. The biological device is a biological material which has a specific discrimination ability, such as microorganisms, cells, tissues, enzymes, antigens, and antibodies. The membrane device is generally a polymer material for fixing the biological device and for screening interference substances. The transducer includes electrodes, an ion selection field effect transistor, a thermal-sensitive resistor, a thermistor, a piezoelectrical device, optical fibers, a phototube, and a sound wave counter. A peroxidase electrode is one of the most popular transducers for biosensors.

Taking biosensors in detecting blood sugars for example, glucose oxidase is fixed on a membrane which is tightened on the surface of a columnar peroxidase electrode. Then polarization potentials are applied to a platinum anode and a silver/silver chloride cathode. The glucose oxidase will catalyze glucose to produce hydrogen peroxide. The hydrogen peroxide is further oxidized to water near the anode surface and then releases electrons. The released electrons are used for calculating glucose concentrations in samples.

The foregoing columnar electrode has the following drawbacks of requiring to be polished frequently, being hard to tie the membrane and being difficult to clean. It further has the following disadvantages of being subject to cross contamination and being hard to calibrate. Furthermore, it is difficult to be produced in a disposable form and it requires high production costs. Practically, it is not convenient in use. Hence, test strip electrodes are developed to overcome the disadvantages of the columnar electrode and are favorable for industrial production.

U.S. Pat. No. 5,120,420 discloses a biochemical detecting electrode strip, including an electrode portion, an insulating layer, a reaction layer, and a sample receiving space which is formed by laying a resin board and a hydrophilic cover on the reaction layer. The space includes a sample inlet and an air outlet. The reaction layer is formed by sequentially coating a carboxymethylcelullose (CMC) solution on an electrode base board, drying the CMC layer, spraying a glucose oxidase solution (GOD) and drying thereof, and spreading an organic suspension which contains a conductive medium and drying thereof to form a biochemical reaction area. The biochemical detecting electrode strip is finished by laying the resin board and the hydrophilic cover for forming the sample receiving space on the base board.

The biochemical detecting electrode strip has the following disadvantages. First, three steps are required in forming the reaction layer, i.e. forming the CMC layer to improve hydrophilic property of the carbon electrode surface, forming the GOD layer, and forming the conductive medium. Each step requires a subsequent drying step. The process is complex. Second, there is only one sampling inlet. The sample is introduced into the reaction area through contacting with an electrode strip tip.

U.S. Pat. No. 5,628,890 discloses another biochemical detecting electrode strip, including an electrode portion, an insulating layer, a reaction layer, one double layer of hydrophilic mesh on the reaction layer, and a covering layer on the mesh layers. The electrode portion includes three electrodes, in which a carbon layer is first printed and then a silver layer is printed thereon. A bioactive substance, silver/silver chloride and conductive medium are disposed on a working electrode, reference electrode and counter electrode in the reaction area. Then the double layer of mesh is disposed on the reaction area, wherein the mesh layer should be hydrophilic for sample access to the reaction area. A blood sample in the hydrophilic mesh layers will be restricted on the reaction layer because of hydrophilic affinity. Then the covering layer is pasted on the mesh layers and leaves a sampling inlet therein. The above detecting electrode strip has the following disadvantages of being complex, and requiring multiple mesh layers and hydrophilic processing. In addition, there is only one sampling inlet and it is hard to determine if samples are accurately incorporated in the reaction area. In addition, the blood sample demands are, as high as more than 10 $\mu L$

SUMMARY OF THE INVENTION

The present invention is to overcome the disadvantages of the prior art and to provide an effective biosensor which is simple in production and detection. Reactive substances are mixed and introduced to a reaction layer in one step. A reticular covering layer is disposed on a sample inlet for producing capillary attraction between the reticular covering layer and the reaction layer. The reticular covering layer and a resulting capillary attraction facilitate sampling when a sample is introduced from an opening end on a side of the biosensor. For example, if the reticular covering layer is hydrophilic, a sample can be introduced from top of the biosensor by hydrophilic affinity.

It is an object of the present invention to provide a biosensor which has multiple sampling sites. The sample can be introduced into the reaction area in more than one direction and the sample demands can be reduced as low as possible. The way of sampling can be achieved by dropping a sample on the biosensor, or approaching the biosensor to a sample, for example, a drop of blood on an earlap.

It is another object of the present invention to provide a biosensor which can introduce a sample to the reaction layer readily and rapidly. The sample can be effectively obtained for detection.

It is a still object of the present invention to provide a biosensor which can reduce sample demands. A blood sample demand can be as low as 5 μL. The pain of a patient can be lessened.

It is a further object of the present invention to provide a biosensor which does not require several drying steps and can form on a surface a uniform and flat reaction layer. It is simple in production and can meet the requirement for accuracy.

To achieve the above objects and avoid the disadvantages of the prior art, the present invention discloses a biosensor for detecting contents of biochemical components in a sample, comprising:

an electrically insulating substrate;
an anode disposed on said substrate wherein said anode is formed with, on both ends of the anode, a working electrode and an anode connector respectively;
a cathode disposed on said substrate wherein said cathode is formed with, on both ends of the cathode, a reference electrode and a cathode connector respectively;
a reaction layer disposed on said working electrode and said reference electrode, wherein said reaction layer and said electrodes form a reaction area for reacting with the sample;
an electrically insulating layer disposed on said substrate and having an opening for receiving the sample and an opening end wherein said insulating layer overlays the portion of said electrodes in the non-reaction area and said opening exposing a portion of the reaction area; and
a reticular covering layer which covers said opening of said insulating layer wherein said reticular layer and said insulting layer form a sampling area from said reticular covering area to the edge of said test strip.

The sample can be introduced to the reaction layer from the top of the reticular covering layer, or from the opening end by a capillary attraction between the reticular covering layer and the reaction layer. The reaction layer is made of a formula including an enzyme, a carrier, an electrical medium and a surfactant.

The reticular covering layer of the present invention is a hydrophilic reticular material or hydrophobic reticular material or metal wire mesh, which provides a capillary attraction to readily and effectively introduce the sample from the top of the reticular covering layer or the opening end on a side of the biosensor to the reaction layer for detection.

The opening end serves as a sample contact point, which can approach a patient for sampling. The sample can be introduced from the opening end to the reaction layer for detection. Simply by approaching and contacting the patient, the biosensor can effectively secure the sample. It is handy in sampling. In a preferred embodiment, the substrate further has an indentation, a notch or a protruding under said opening end in said insulating layer as a sample contact point.

By the disclosure of the invention, several advantages will be obtained. A biosensor manufacturer can produce biosensors in a more convenient way, an analyst can obtain samples in a more convenient and effective way, and a patient can reduce his/her inconvenience to a minimum. Meanwhile, an accurate detection result can be obtained.

The foregoing and other objects and advantages of the invention and the manner in which the same are accomplished will become clearer based on the following detailed description taken in conjunction with the accompanying drawings.

DETAILED DESCRIPTION OF THE INVENTION

Figure 1:
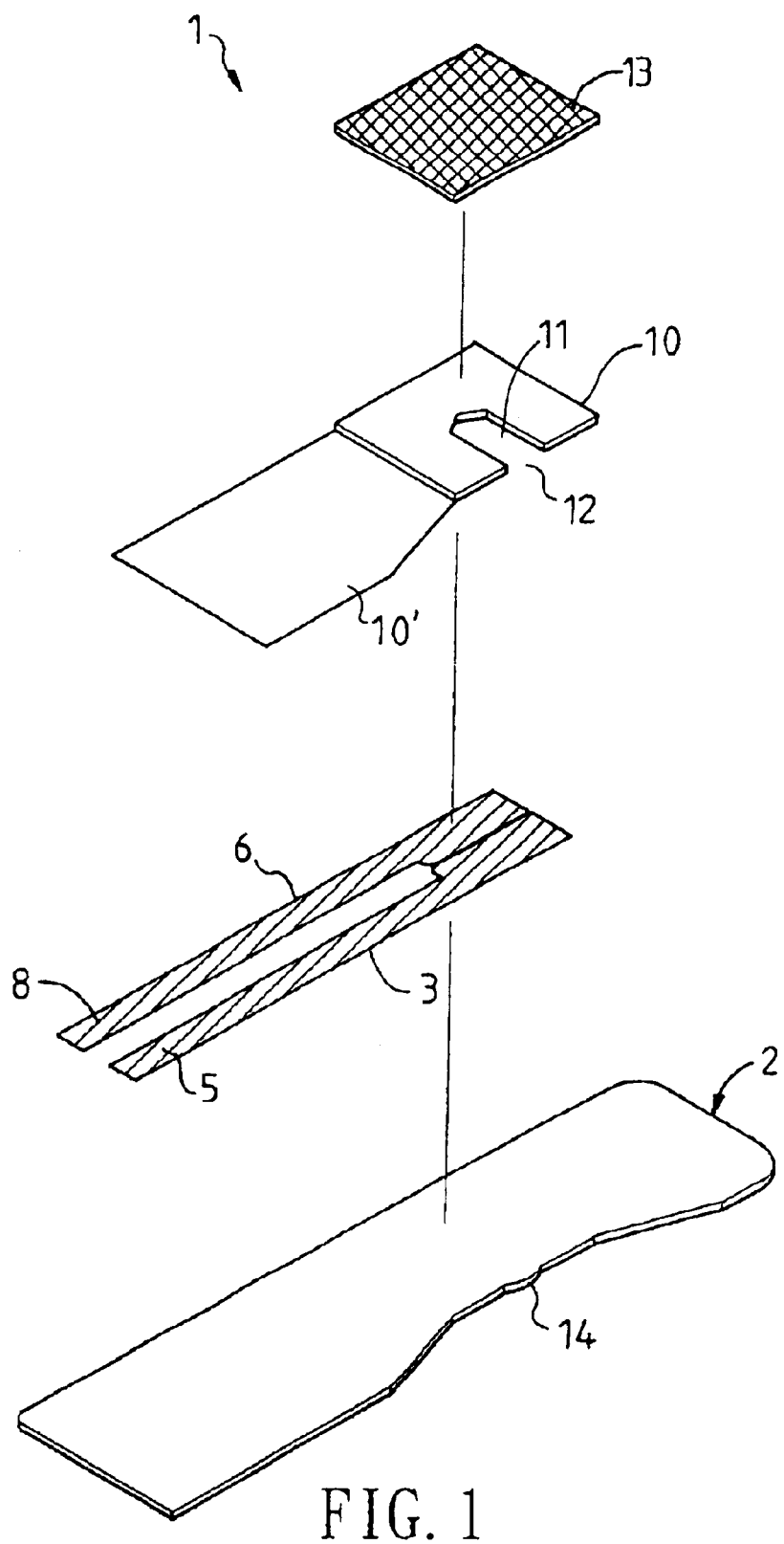
FIG. 1 is an exploded view of the biosensor according to an embodiment of the invention.
Figure 2:
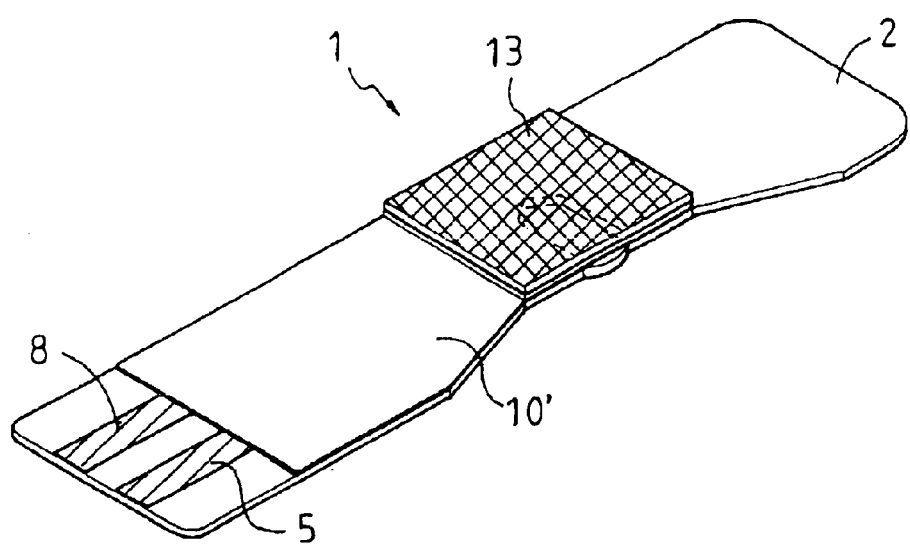
FIG. 2 is perspective view of the biosensor of FIG. 1.
Figure 3:
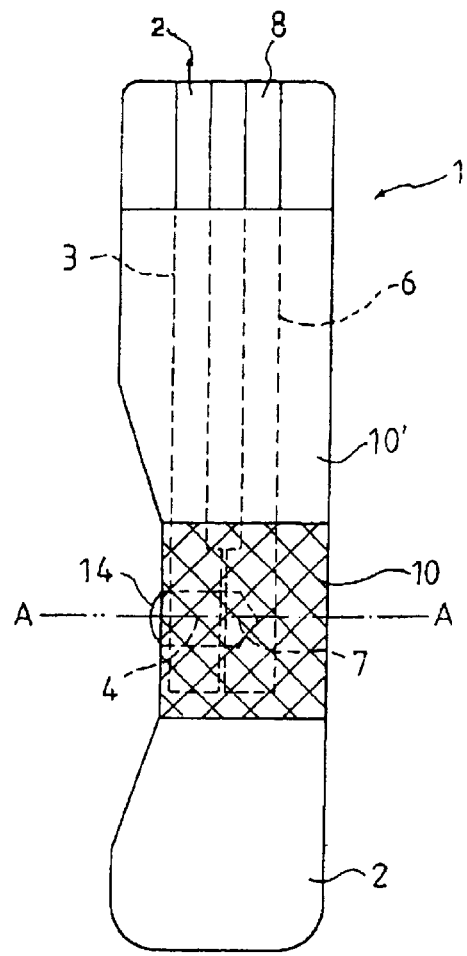
FIG. 3 is a top view of the biosensor of FIG. 1.

With reference to FIGS. 1 to 4, a biosensor 1 according to an embodiment of the invention for detecting contents of biochemical components in a sample includes: an electrically insulating substrate 2; an anode 3 disposed on the substrate 2, the anode 3 provided with working electrodes 4 (as shown in FIG. 3) and an anode connector 5 at both ends of the anode 3 respectively; and a cathode 6 disposed on the substrate 2, wherein the cathode 6 is provided with reference electrodes 7 (as shown in FIG. 3) and a cathode connector 8 at both ends of the cathode 6 respectively.

The substrate 2 is electrically insulated and has a flat surface. The substrate 2 should be thermally resistant under temperatures ranging from 40° C. to 200° C. in a thermal process which is used for increasing conductance and adherence of the anode 3 and cathode 6. Materials suitable for the substrate 2 include, but not limited to, a polyvinylchloride, polyester, Bakelite plate, fiberglass (FR-4), polyethylene terephthalate, polycarbonate, polypropylene PP, polyethylene, PA, PS, glass, and ceramics (CEM-1). Preferably, said substrate further has an indentation, a notch or a protruding under the opening end in the insulating layer of the biosensor serving as a sample contact point. More preferably, the protruding is semicircular. Such indentation, notch or protruding not only is distinguishable and can get closer to the sample for making the sampling easier, but also can lessen the feeling of a patient.

The anode 3 and the cathode 6 are made of two spaced-apart conductive films to be connected to a detection device (not shown in the figures).

Figure 4:
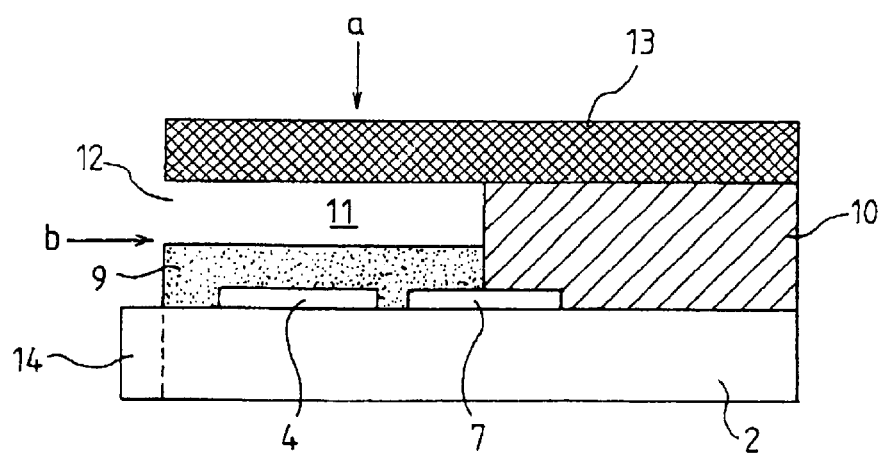
FIG. 4 is a sectional view of the biosensor taken from line A—A of FIG. 3.

After partially covered by electrically insulating layers 10 and 10', the anode 3 is formed with, at both exposed ends of the anode, an anode connector 5 for connecting the detection equipment and a working electrode 4 on which a bioactive layer is disposed, i.e. a reaction layer 9 (please refer to FIG. 4). The working electrode 4 is used for transmitting electrical signals induced by chemical or biochemical reactions of the sample to the detection device. After covered by the electrically insulating layers 10 and 10', the cathode 6 is formed with, respectively on both exposed ends, a cathode connector 8 for connecting the detection device and the reference electrode 7 (please refer to FIG. 3) on which a reaction layer 9 is disposed. The reference electrode 7 is used in cooperation with the working electrode 4 for detecting the electrical signals from the samples.

The biosensor 1 of the invention further comprises a reaction layer 9 on the working electrode 4 and the reference electrode 7. The reaction layer 9 is a bioactive layer and is used for contacting the sample to produce chemical reactions. The reaction layer 9 does not overlap the electrically insulating layer 10.

The reaction layer 9 is formed by disposing a formula of bioactive substances on a part of the substrate 2, the anode 3 and the cathode 6. The formula of the reaction layer comprises an enzyme, a carrier, an electrical medium and a surfactant. In an embodiment, the carrier is 0.05 weight percent to 1.5 weight percent of the formula. The carrier includes micro cellulose, methylcellulose, carboxylmethylcellulose, starch, vinylalcohol, vinylpyrrolidone, PVA, PVP, PEG, or gelatin. A useful formula is described as follows:

An enzyme, such as a glucose oxidase, with a dosage of about 200 to 1200 U/ml;

An enzyme preservative, with a dosage of about 0.1 to 1.0 weight percent of the formula, wherein the preservative may include albumin, dextrin, dextran, or ammo acids, which may be applied individually or in combination;

An electrical medium, with a dosage of 2.0 to 10.0 weight percent of the formula, wherein the useful electrical medium includes potassium ferricyanide; and A surfactant, with a dosage less than 0.1 weight percent of the formula, wherein the useful surfactant includes polyethylene glycol alkyl phenyl ether (Triton X-100), Triton X-405, Triton X-114, sodium lauryl sulfate, polyoxyethylenesorbitan monolaurate (Tween 20), Tween 40, Tween 60, Tween 80, or other water-soluble surfactant or detergent.

The biosensor 1 of the present invention further comprises electrically insulating layers 10 and 10' on the substrate 2, which has an opening 11 (with a height of about 0.25 to 0.3 mm) for receiving the sample in the reaction layer 9 and an opening end 12. The insulating layer overlays the portion of said electrodes in the non-reaction area and said opening exposing a portion of the reaction area. The electrically insulating layers 10 and 10' are made of PP, PVC, PET, PC, PE, or other insulating plastic materials.

After the electrically insulating layer 10 and 10' are disposed on the substrate 2, the exposed ends of the anode 3 and the cathode 6 are respectively formed, at one end, with an anode connector 5 and a cathode connector 8, and on the other end within a region confined by the opening 11 a working electrode 4 and a reference electrode 7 are formed. In a preferred embodiment, the working electrode 4 has an area same as that of said reference electrode or said working electrode 4 has a smaller or larger area than that of the reference electrode 7.

A reaction area for receiving the sample to react refers to an area confined by the opening 11 and the reaction layer 9 which is under the opening 11. The thickness of the electrically insulating layer 10 disposed on the reaction area is generally 0.25 mm to 0.3 mm. In addition, the biosensor of the invention can further comprises a separating layer with an opening which is disposed on and overlays said insulting layer wherein said separating layer and said insulating layer form a space, wherein said opening overlays said opening in said insulating layer. The separating layer and the insulating layer form a space to provide a function in receiving sample.

The biosensor 1 of the invention comprises a reticular covering layer 13 for protecting the reaction layer 9 and for increasing capillarity with the sample on the electrically insulating layer 10. The reticular covering layer 13 covers at least a part of the opening 11. The reticular layer and the insulting layer form a sampling area from said reticular covering area to the edge of said test strip. Therefore, the sample can be introduced into the space formed by the reticular covering layer and the electrically insulating layer in any directions and then readily reaching the reaction area. A sample can be received on the reaction layer 9 from the opening end 12 by the capillary attraction between the reticular covering layer 13 and the reaction layer 9.

The reticular covering layer 13 is made of a hydrophilic reticular material or a hydrophobic reticular material or metal wire mesh. The screen of the mesh is, but not limited to, 60 to 300 screens. As shown in FIG. 4, the sample can be introduced into the biosensor of the invention from the direction 'a' or 'b'. More preferably, when the reticular covering layer 13 is made of a hydrophilic reticular material, a hydrophilic sample can be introduced from the opening end 12, or from the top of the reticular covering layer in the direction 'a' of FIG. 4. When the reticular covering layer 13 is made of a hydrophobic reticular material, a hydrophilic sample, having less affinity, is introduced from the opening end 12 through capillarity. The reticular covering layer 13 can also be a hydrophobic reticular material which is processed by a surfactant, plasma or corona. Preferably, the surfactant is selected from X-100, Triton X-405, Triton X-114, sodium lauryl sulfate, polyoxyethylenesorbitan monolaurate (Tween20), Tween40, Tween60, Tween80, and other water-soluble surfactant or detergent.

Preferably, the biosensor 1 of the invention has two ways of introducing a sample to the reaction layer 9. When the reticular covering layer 13 is hydrophilic, samples can be introduced in a first sample introduction direction 'a' of FIG. 4 by a hydrophilic attraction provided by the hydrophilic reticular covering layer 13, or a sample can be introduced from a second sample introduction direction 'b' of FIG. 4 by a capillary attraction. In the direction 'b', the biosensor 1 can directly approach the sample and the sample can be rapidly and sweepingly attracted to the reaction layer 9. Not only detection results can be ensured, but also the sample demands can be reduced. Furthermore, when the reticular covering layer 13 is hydrophobic, a sample can be introduced in the second sample introduction direction 'b' into the reaction layer 9. This is done by approaching the biosensor 1 to a patient. For example, the patient's ear is pierced by a lancet to produce a blood droplet and then the biosensor 1 is approached to the blood droplet which is to be introduced to the reaction layer 9 in the second sample introduction direction 'b'. Thus, the sample demands can be reduced as low as possible.

Figure 14:
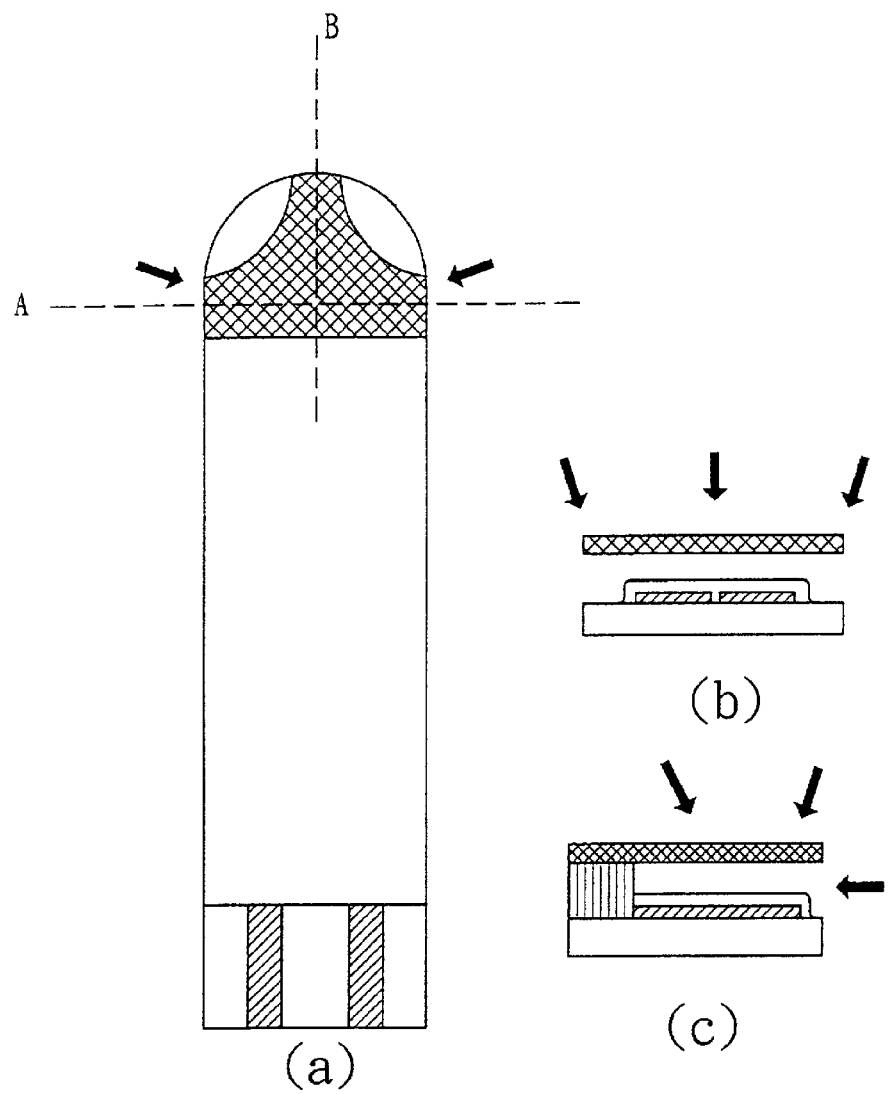
Figure 15:
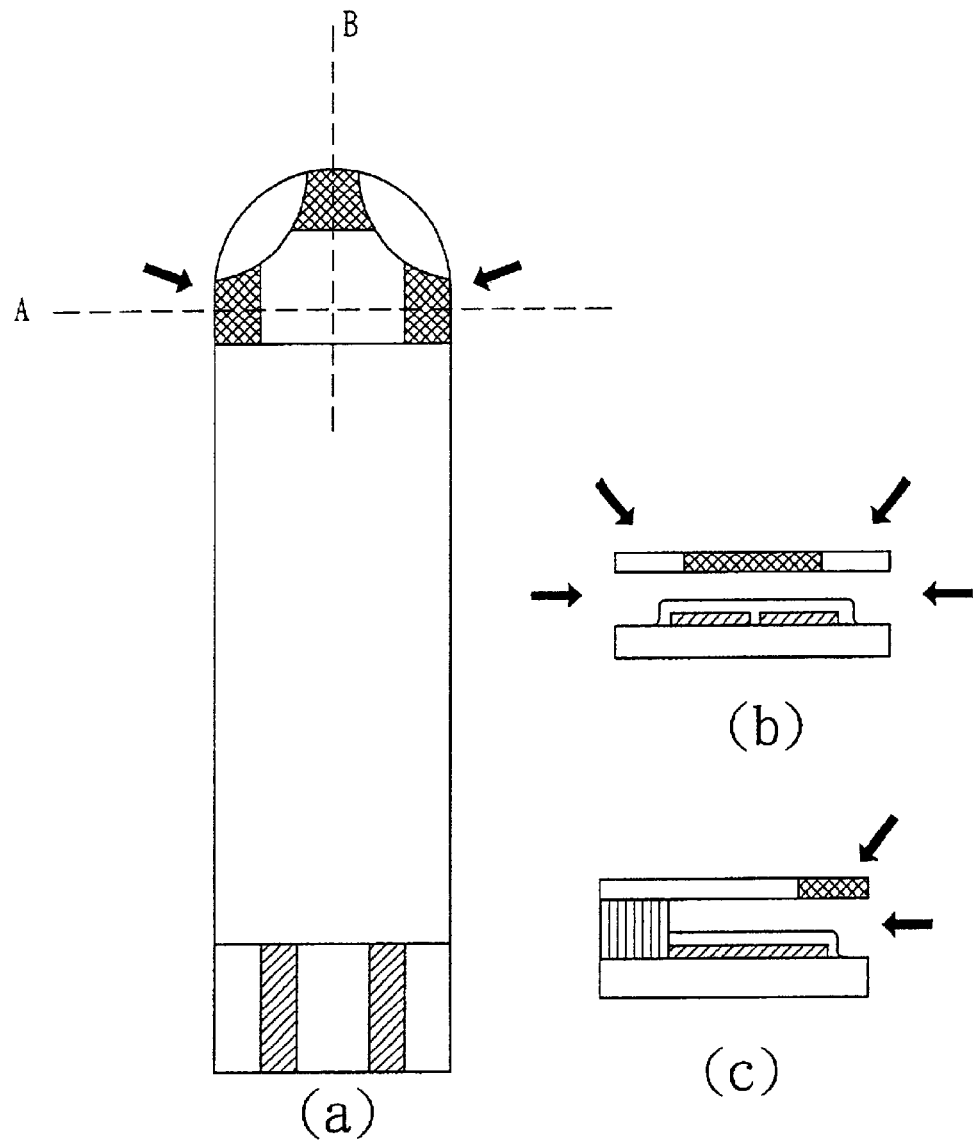
Figure 16:
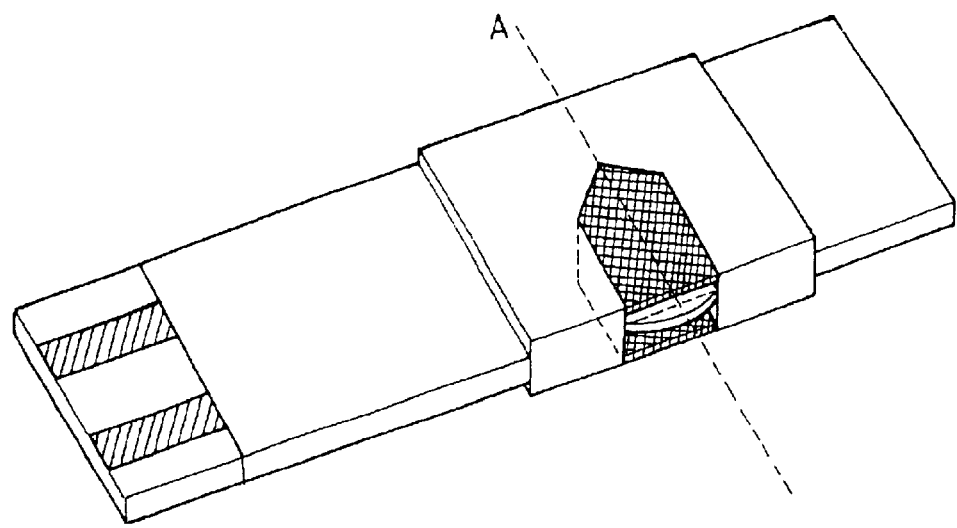
FIG. 16 is a three-dimensional plot of the biosensor according to the invention.
Figure 16:
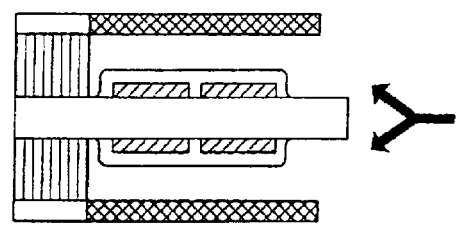
Figure 16:
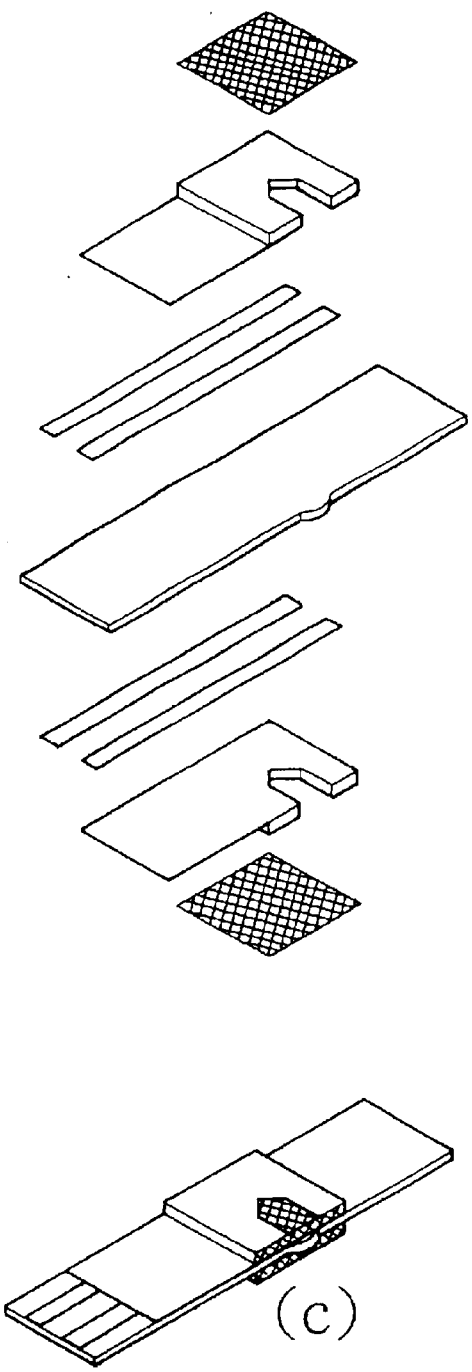

FIGS. 6 to 15 show the preferred embodiments illustrating that the biosensor according to the invention has a variety of appearances. In FIGS. 6 to 13, plot (a) shows the top view of the biosensor according to the invention, plot (b) shows the sectional view of the biosensor taken from line A of the plot (a) and the arrows in the plots show the directions for introducing the sample. In FIGS. 14 and 15, plot (a) shows the top view of the biosensor according to the invention, plot (b) shows the sectional view of the biosensor taken from line A of the plot (a), plot (c) shows the sectional view of the biosensor taken from line B of the plot (a), and the arrows in the plots show the directions for introducing the sample. FIG. 16 shows a three-dimensional plot of the biosensor according to the invention wherein plot (a) shows the appearance of the biosensor, plot (b) shows the sectional view of the biosensor taken from line A of the plot (a) and the arrow in plot (b) shows the directions for introducing the sample.

Blood samples from a diabetic are required for being applied to blood sugar test strips. Especially, for a patient who is seriously ill, frequent blood samplings are required to monitor the patient in one day. If blood demands can be reduced, a finer lancet can be applied and the hurts and pains of the patient can be reduced to a minimum. Furthermore, the blood sample needs to be wiped in applying the sample to a conventional test strip if sample amount is not enough and which may result in measurement errors. The invention can reduce the blood demands and can improve conventional sampling methods.

In a preferred embodiment, the substrate 2 of the biosensor 1 further has a semicircular protruding portion 14 under the opening end 12 to serve as a sample contact point. The semicircular protruding portion 14 allows the biosensor 1 to get more closer to a sampled point and facilitates sampling, and helps to lessen patient's sense when the biosensor contacts the patient.

Different from the prior U.S. Pat. Nos. 5,120,420 and 5,628,890, the present invention adopts a single layer of reticular material on the reaction layer. Since there are many screens of the reticular material on the opening end 12 of the reaction area, capillarity will occur and sampling is facilitated. Both hydrophilic or hydrophobic reticular materials can be applied onto the reaction area of the biosensor. When the reticular covering layer 13 is hydrophobic, a sample can be introduced in the direction 'b'; when the reticular covering layer 13 is hydrophilic, a sample can be introduced in both the directions 'a' and 'b'.

The process of producing the electrode test strip of the biosensor of the invention is simplified and the quality of the strip is improved. The production steps are summarized as follows.

Step 1.

A layer of conducting film which includes an anode 3 and a cathode 6 is printed on any one flat surface of a flat plate substrate 2 by screen printing. The conducting film is made of conductive ink which is suitable for screen printing, such as carbon ink, silver ink, gold ink, a combination of silver and carbon inks, or any combinations of these inks. For example, the silver ink is printed and then carbon ink. The conducting film is then dried at a temperature of 40° C. to 150° C.

Step 2.

A 0.1 to 1.0 mm thick electrically insulating layer 10' is disposed by film pasting technology on the side on which the conducting film is printed. A 0.25 to 0.3 mm thick electrically insulating layer 10 which has an opening 11 and an opening end 12 is disposed on the reaction area. The working electrode 4 and the reference electrode 7 are formed by keeping the conducting film partly exposed and the electrodes 4 and 7 are restricted in an area confined by the opening 11. The area formed by the working electrode 4 and the reference electrode 7 is referred to herein as a reaction area.

Step 3.

Bioactive substances are dropped on the reaction area and dried at a temperature of 40° C. to 60° C. to form a reaction layer 9.

Step 4.

A reticular covering layer 13 is disposed on the reaction layer 9.

The present invention is described in detail in accordance with the following embodiments.

EXAMPLE 1

A conducting film of carbon ink is screen printed on a flat surface of a PC board substrate 2 to form an anode 3 and a cathode 6 which are independently isolated. The substrate 2 is dried at a temperature of 130° C. Then, a 0.27 mm thick PET electrically insulating layer is disposed on the flat surface to form an anode connector, a cathode connector, a working electrode and a reference electrode by keeping the conducting film partly exposed. The area formed by the working electrode and the reference electrode is the reaction area.

Then a composition of the following formula is dropped on the surface of the reaction area to form a reaction layer:

| | |
|---|---|
| glucose oxidase | 0.63% |
| albumin | 0.5% |
| potassium ferricyanide | 6% |
| methyl cellulose | 0.5% |
| Triton X-100 (t-Octylphenoxypolyethanol) | 0.07% |
| phosphate buffer (pH = 5.0) | 92.30% |

After the above formula of bioactive substances on the reaction area is added, the test strip is dried at a temperature of 50° C. for 15 minutes. Then a reticular covering layer (Teterlon, T120-54) is disposed on the reaction layer and the current electrode test strip of the biosensor is finished.

Figure 5:
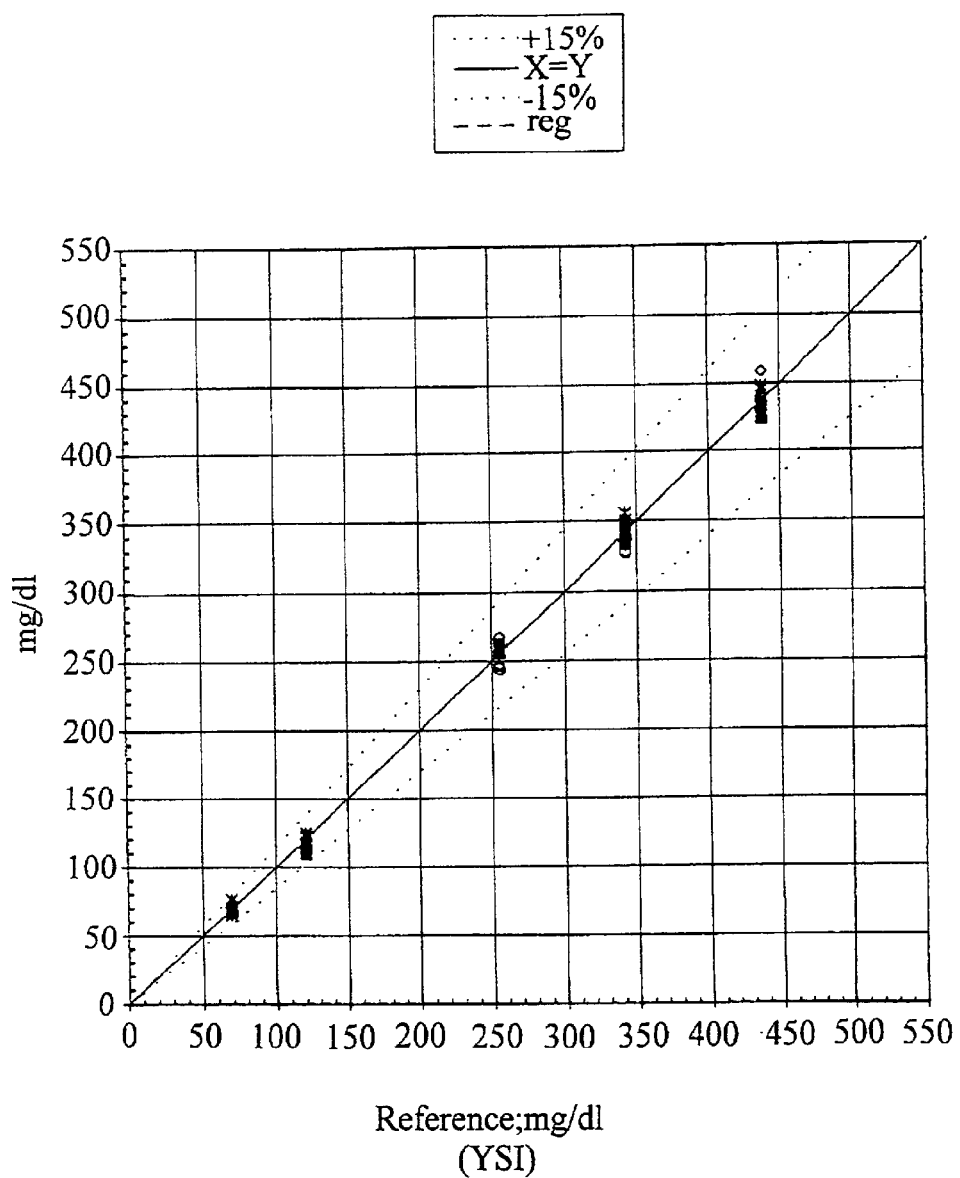
FIG. 5 is a comparison chart of blood glucose concentrations between the detecting result of the biosensor according to the invention and that of an YSI glucose analyzer.
Figure 6:
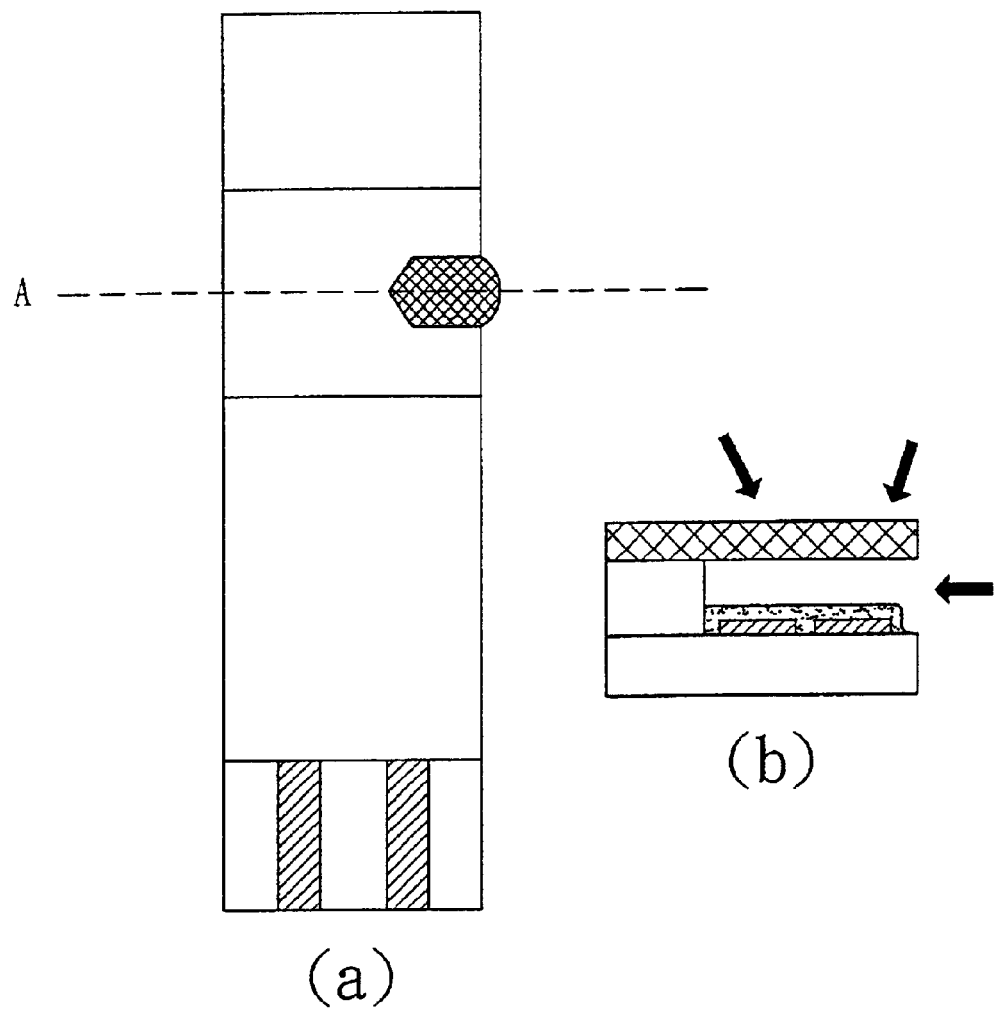
FIGS. 6–15 show the biosensors according to the invention having a variety of appearances wherein (a) is a top view of the biosensor and (b) is a sectional view of the biosensor.
Figure 7:
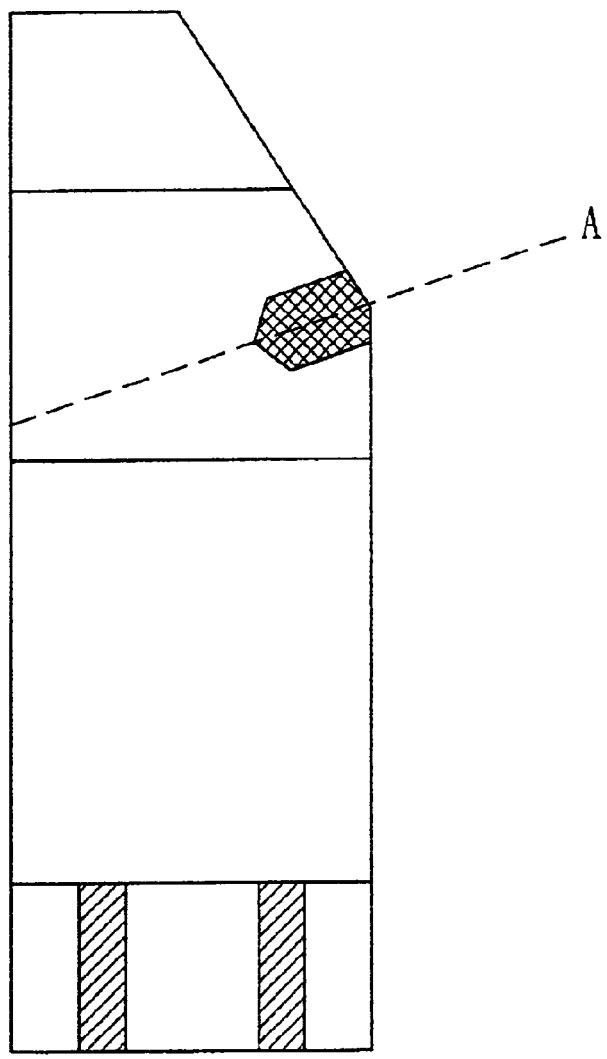
Figure 8:
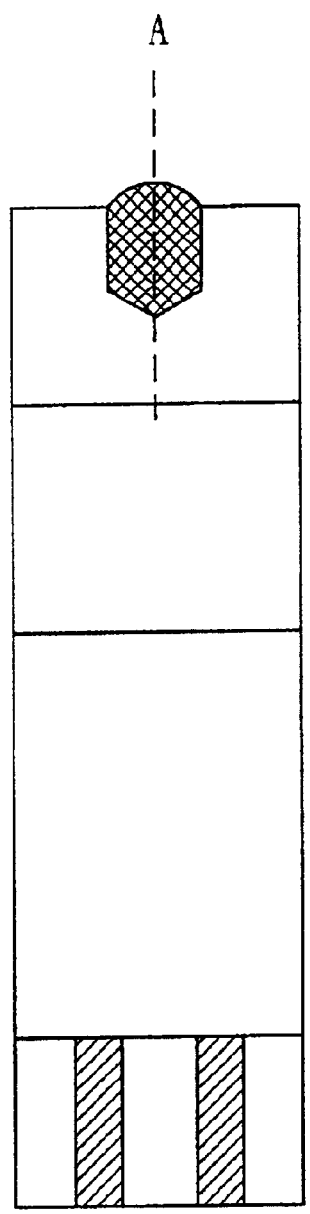
Figure 9:
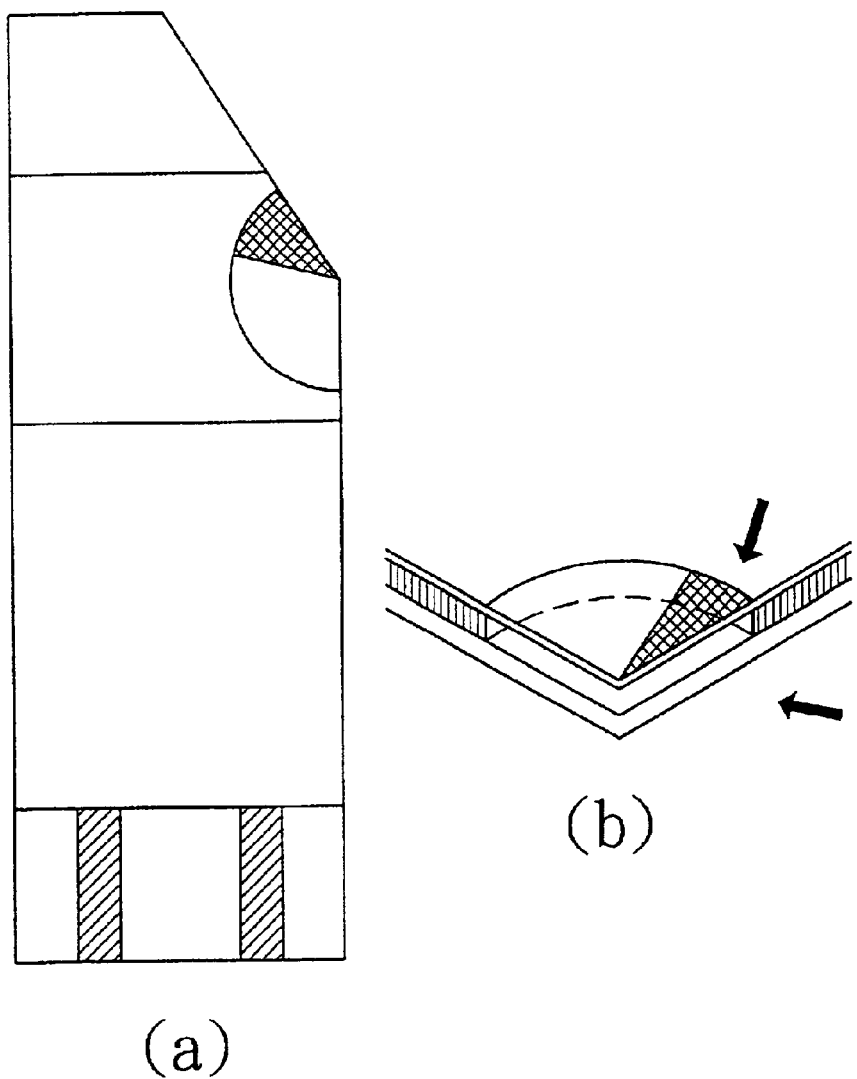
Figure 10:
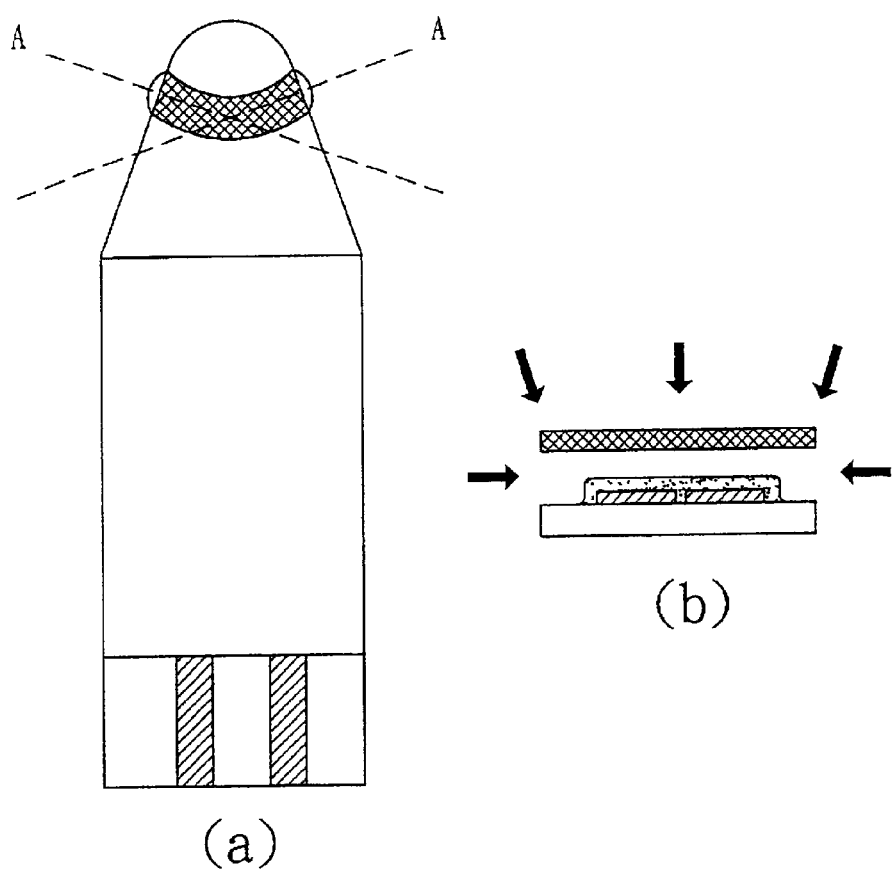
Figure 11:
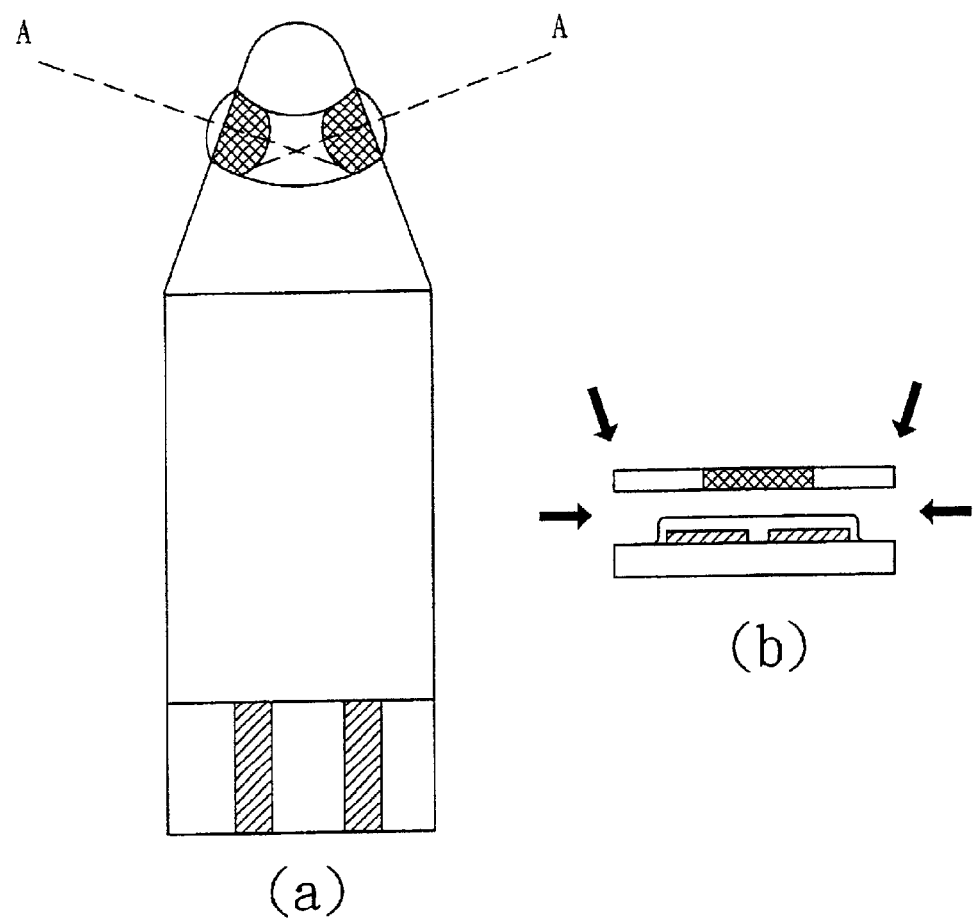
Figure 12:
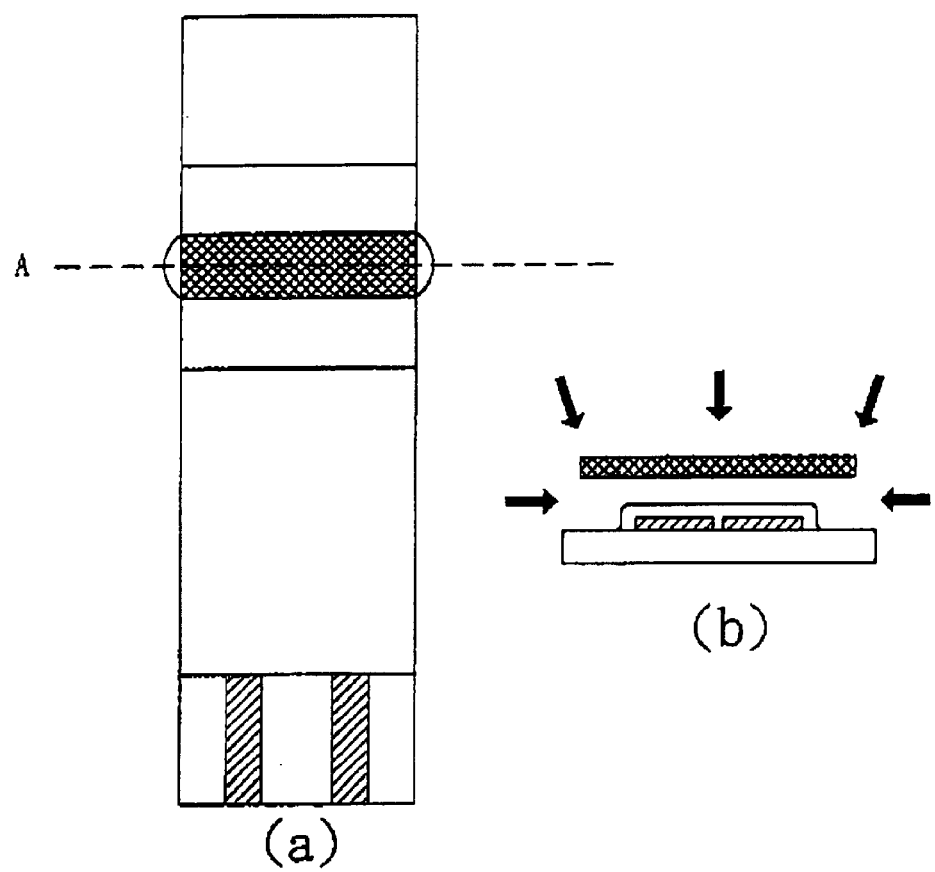
Figure 13:
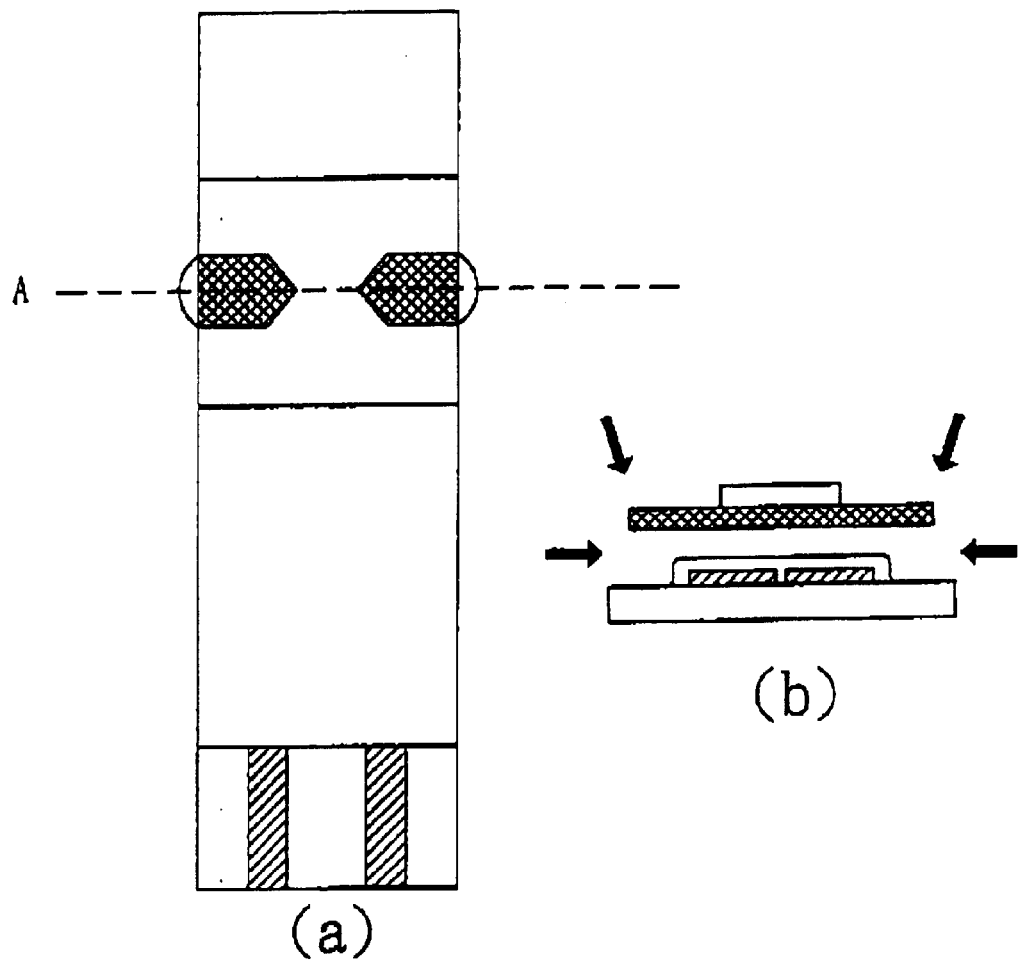

A disposable current electrode test strip is thus produced and can introduce samples is the direction 'b' as shown in FIG. 4, and can detect the blood sugar by taking whole blood as a sample. The results are shown in FIG. 5, a comparison chart of blood sugar concentrations between the result of the biosensor according to the invention and that of an YSI blood sugar analyzer. The coefficient of variation of the test strip according to the invention is lower than 5%. The blood demand for detection is less than 4 μL. The results show an accurate measurement performed by the biosensor according to the present invention.

EXAMPLE 2

Example 2 is almost the same as Example 1, except that the formula is changed as follows:

| | |
|---|---|
| glucose oxidase | 0.63% |
| albumin | 0.5% |
| potassium ferricyanide | 6% |
| carboxymethyl cellulose | 0.5% |
| Triton X-100 (t-Octylphenoxypolyethanol) | 0.07% |
| phosphate buffer (pH = 5.0) | 92.30% |

EXAMPLE 3

Example 3 is almost the same as Example 1, except that the formula is changed as follows:

| | |
|---|---|
| glucose oxidase | 0.63% |
| albumin | 0.5% |
| potassium ferricyanide | 6% |
| dextran | 0.5% |
| Triton X-100 (t-Octylphenoxypolyethanol) | 0.07% |
| phosphate buffer (pH = 5.0) | 92.30% |

EXAMPLE 4

Example 4 is almost the same as Example 1, except that the formula is changed as follows:

| | |
|---|---|
| glucose oxidase | 0.63% |
| albumin | 0.5% |
| potassium ferricyanide | 6% |
| glutamic acid | 0.1% |
| PEG | 0.3% |
| Tween 20 (polyoxyethylenesorbitan monolaurate) | 0.1% |
| phosphate buffer (pH = 6.0) | 92.37% |

EXAMPLE 5

Example 5 is almost the same as Example 1, except that the reticular covering layer is replaced by a hydrophobic polyester PES-37T. The production steps are the same as those illustrated in Example 1. After a reaction layer is formed, the reticular material PES-37T is pasted on the electrically insulating layer and a test strip is finished.

EXAMPLE 6

Example 6 is almost the same as Example 1, except that the reticular covering layer is replaced by a stainless wire mesh. The production steps are the same as those illustrated in Example 1. After a reaction layer is formed, the stainless wire mesh is pasted on the electrically insulating layer and a test strip is finished.

EXAMPLE 7

Example 7 is almost the same as Example 1, except that the PVC board is replaced by a PC board and that the covering layer is replaced by a hydrophobic reticular polyester PES-42T. The production steps are the same as those illustrated in Example 1. After a reaction layer is formed, the reticular PES-42T is pasted on the electrically insulating layer and a test strip is finished.

EXAMPLE 8

Example 8 is almost the same as Example 1, except that the reticular covering layer is replaced by a hydrophobic reticular material PET-43T. The PET-43T is soaked and processed by 1% of Triton X-100 to become hydrophilic. The production steps are the same as those illustrated in Example 1. After a reaction layer is formed, the reticular material PET-43T is pasted on the electrically insulating layer and a test strip is finished. Samples can be introduced in the directions 'a' or 'b' as shown m FIG. 4.

The disclosed biosensor of the present invention not only includes advantages of simplicity in production and accuracy in detection, but also includes multiple sampling sites. Samples can be dropped to release, or the biosensor can approach to samples for facilitating sampling. A sample can be easily and rapidly introduced to the reaction layer. Furthermore, the pains of a patient can be lessened by reducing sample demands. This invention provides a convenient and effective solution for manufacturers, analyst and patients.

The methods and features of this invention have been sufficiently described in the above examples and descriptions. It should be understood that any modifications or changes without departing from the spirits of the invention are intended to be covered in the protection scopes of the invention.

What is claimed is:

1. A biosensor for detecting contents of biochemical components in a sample, comprising:
   an electrically insulating substrate;
   a working electrode disposed on said substrate;
   a reference electrode disposed on said substrate which is spaced from said working electrode;
   a reaction layer disposed on said working electrode and said reference electrode, wherein said reaction layer and said electrodes form a reaction area for reacting with the sample;
   an electrically insulating layer disposed on said substrate and having an opening for receiving the sample, wherein said opening exposes a portion of said reaction area and the end of said opening is located at the edge of the biosensor; and
   a reticular covering layer which covers said opening and an end of said opening of said insulating layer, wherein said reticular layer and said insulting layer form a sampling area from said reticular covering area to an edge of the biosensor.

2. The biosensor of claim 1, wherein said substrate further has an indentation, a notch, or a protrusion, serving as a sample contact point, under the end of said opening in said insulating layer.

3. The biosensor of claim 1, wherein said working electrode has a size the same as, smaller than or larger than that of said reference electrode.

4. The biosensor of claim 1, wherein said reaction layer is made of a formula comprising an enzyme, a carrier, an electrical medium and a surfactant.

5. The biosensor of claim 4, wherein said carrier is a micro cellulose, methyl cellulose, carboxylmethyl-cellulose, starch, vinyl alcohol, vinyl pyrrolidone, PVA, PVP, PEG, or gelatin.

6. The biosensor of claim 4, wherein said carrier ranges from 0.05 weight percent to 1.5 weight percent of the formula.

7. The biosensor of claim 4, wherein said electrical medium is potassium ferricyanide.

8. The biosensor of claim 4, wherein said surfactant is Triton X-100, Triton C-405, Triton X-114, sodium lauryl sulfate, polyoxyethylenesorbitan monolaurate (Tween 20), Tween 40, Tween 60, Tween 80, or other water-soluble surfactant or detergent.

9. The biosensor of claim 4, wherein said surfactant ranges from less than 0.1 weight percent of the formula.

10. The biosensor of claim 1, wherein said electrically insulating layer is polypropylene, polyvinylchloride, polyethylene terephthalate, polycarbonate, polyethylene, or other insulating plastic materials.

11. The biosensor of claim 1, wherein said electrically insulating layer has a thickness from 0.25 to 0.35 mm.

12. The biosensor of claim 1, which further comprises a separating layer with an opening which is disposed on and overlays said insulting layer wherein said separating layer and said insulating layer form a space, wherein said opening in said separating layer overlays said opening in said insulating layer.

13. The biosensor of claim 1, wherein said reticular covering layer is made of a hydrophilic reticular material or a hydrophobic reticular material or metal wire reticular material.

14. The biosensor of claim 1, wherein the reticular covering layer has 60 to 300 meshes.

15. The biosensor of claim 1, wherein the reticular covering layer is a hydrophobic reticular material which is optionally processed by a surfactant, plasma or corona.

16. The biosensor of claim 15, wherein the surfactant is Triton X-100, 5 Triton X-405, Triton X-114, sodium lauryl sulfate, polyoxyethylenesorbitan monolaurate (Tween20), Tween40, Tween60, Tween80, or other water-soluble surfactant or detergent.

* * * * *